United States Patent
Benneker et al.

(10) Patent No.: US 7,408,081 B2
(45) Date of Patent: *Aug. 5, 2008

(54) PROCESS FOR TREATING AN AQUEOUS MEDIUM CONTAINING CYCLOHEXANONE OXIME AND CYCLOHEXANONE

(75) Inventors: Arno Benneker, Geleen (NL); Henk Oevering, Elsloo (NL); Johannes A. L. Brouwers, Echt (NL)

(73) Assignee: DSM IP Assets B.V., Heerlen (NL)

( * ) Notice: Subject to any disclaimer, the term of this patent is extended or adjusted under 35 U.S.C. 154(b) by 233 days.

This patent is subject to a terminal disclaimer.

(21) Appl. No.: 10/496,873

(22) PCT Filed: Dec. 4, 2001

(86) PCT No.: PCT/NL01/00884

§ 371 (c)(1),
(2), (4) Date: Nov. 17, 2004

(87) PCT Pub. No.: WO03/048110

PCT Pub. Date: Jun. 12, 2003

(65) Prior Publication Data

US 2005/0065375 A1    Mar. 24, 2005

(51) Int. Cl.
*C07C 249/00* (2006.01)
*C07C 251/00* (2006.01)
*C07C 259/00* (2006.01)
*C07C 291/00* (2006.01)

(52) U.S. Cl. ...................... 564/267; 564/259

(58) Field of Classification Search ............... 564/267, 564/259
See application file for complete search history.

(56) References Cited

U.S. PATENT DOCUMENTS

| | | | |
|---|---|---|---|
| 3,720,755 A | 3/1973 | Duyverman et al. | |
| 3,720,758 A | 3/1973 | De Rooij et al. | |
| 3,862,230 A | 1/1975 | De Rooij et al. | |
| 3,940,422 A | 2/1976 | Harita et al. | |
| 3,940,442 A * | 2/1976 | de Rooij | 564/259 |
| 3,948,988 A * | 4/1976 | de Rooij | 564/259 |
| 3,997,607 A * | 12/1976 | de Rooij | 564/259 |
| 4,328,198 A | 5/1982 | van de Moesdijk | |
| 4,994,613 A | 2/1991 | Fruchey | |
| 6,759,556 B2 * | 7/2004 | Blaauw et al. | 564/267 |
| 6,844,469 B2 | 1/2005 | Bennecker et al. | |
| 6,849,765 B2 | 2/2005 | Suzuki et al. | |
| 7,005,547 B2 * | 2/2006 | Blaauw et al. | 564/259 |
| 2005/0038294 A1 * | 2/2005 | Benneker et al. | 564/267 |
| 2006/0079678 A1 * | 4/2006 | Oevering et al. | 540/535 |

FOREIGN PATENT DOCUMENTS

| | | |
|---|---|---|
| DE | 4328795 | 3/1995 |
| EP | 0 005291 | 11/1979 |
| GB | 1138750 | 1/1969 |
| GB | 1283280 | 7/1972 |
| GB | 1284515 | 8/1972 |
| JP | 2002-302475 | 10/1973 |
| JP | 48-035257 | 10/2002 |
| WO | 01/94297 | 12/2001 |
| WO | 01/94298 | 12/2001 |

* cited by examiner

*Primary Examiner*—Yvonne Eyler
*Assistant Examiner*—Chukwuma O Nwaonicha
(74) *Attorney, Agent, or Firm*—Nixon & Vanderhye P.C.

(57) ABSTRACT

The invention relates to a process for treating an aqueous medium containing cyclohexanone oxime and cyclohexanone, said process comprising stripping the aqueous medium with steam, wherein said stripping is carried out at a pressure higher than 0.11 MPa. The invention also relates to a process for the preparation of cyclohexanone oxime, which involves stripping at a pressure higher than 0.11 MPa.

17 Claims, 2 Drawing Sheets

PROCESS FOR TREATING AN AQUEOUS MEDIUM CONTAINING CYCLOHEXANONE OXIME AND CYCLOHEXANONE

CROSS REFERENCE TO RELATED APPLICATION

This application is the National Phase of International Application PCT/NL01/00884 filed Dec. 4, 2001 which designated the U.S., and was published in the English language.

The present invention relates to a process for treating an aqueous medium containing cyclohexanone oxime and cyclohexanone. The invention also relates to a process for preparing cyclohexanone oxime.

Cyclohexanone oxime can be produced in a process in which a buffered, aqueous medium containing buffer acids or acidic salts, for example phosphate buffers, and buffer salts derived from these acids, is continuously recycled between a hydroxylammonium synthesis zone in which nitrate or nitrogen oxide is catalytically reduced with molecular hydrogen to hydroxylammonium, and a cyclohexanone oxime synthesis zone where hydroxylammonium reacts with cyclohexanone to form cyclohexanone oxime. After having been enriched in hydroxylammonium in the hydroxylammonium synthesis zone, the aqueous medium is passed from the hydroxylammonium synthesis zone to the cyclohexanone oxime synthesis zone. The cyclohexanone oxime can then be separated from the aqueous medium that is recycled to the hydroxylammonium synthesis zone. Before the aqueous medium is recycled to the hydroxylammonium synthesis zone, it may be enriched with the required nitrate by addition of nitric acid or by absorption of nitrous gases in the aqueous medium in which instance nitric acid is formed in situ.

The net chemical reactions occurring during the process can be represented by the following equations:
1) Preparation of the hydroxylammonium:

2) Preparation of the oxime:

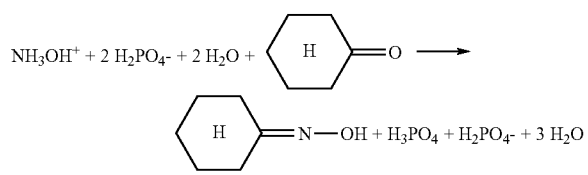

3) Supply of $HNO_3$ to make up the depletion of the source of nitrate ions after removal of the oxime formed:

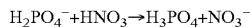

The catalyst used in the preparation of hydroxylammonium is generally palladium and/or platinum on a carrier material of carbon or alumina. The activity of the catalyst is adversely affected by the presence of organic contaminants, such as cyclohexanone and cyclohexanone oxime, present in the recycled stream.

Document U.S. Pat. No. 3,940,442 describes a process wherein an aqueous medium leaving the cyclohexanone oxime synthesis is subjected to a stripping step to remove trace amounts of cyclohexanone oxime before it is recycled to the hydroxylamine synthesis zone in order to prevent poisoning of the catalyst in the hydroxylamine synthesis zone. This stripping step described in U.S. Pat. No. 3,940,442 is performed in a distilling column at atmospheric pressure.

It is now found that the efficiency of the concentration reduction of cyclohexanone and cyclohexanone oxime in the aqueous medium is markedly improved by increasing the pressure.

Accordingly, the invention provides a process for treating an aqueous medium containing cyclohexanone oxime and cyclohexanone, said process comprising stripping the aqueous medium with steam, characterized in that said stripping is carried out at a pressure higher than 0.11 MPa.

The invention also provides a process for preparing cyclohexanone oxime, said process comprising:

passing an aqueous medium containing phosphate from a hydroxylammonium synthesis zone to a cyclohexanone oxime synthesis zone, from the cyclohexanone oxime synthesis zone to a stripping zone and from the stripping zone back to the hydroxylammonium synthesis zone, in said hydroxylammonium synthesis zone, preparing hydroxylammonium by catalytically reducing nitrate or nitrogen oxide with hydrogen;

in said cyclohexanone oxime synthesis zone, preparing cyclohexanone oxime by reacting hydroxylammonium with cyclohexanone;

in said stripping zone, stripping the aqueous medium with steam; characterized in that said stripping is carried out at a pressure higher than 0.11 MPa.

According to the invention the aqueous medium obtained after stripping may have a lower concentration cyclohexanone and cyclohexanone oxime. It is also possible that the aqueous medium to be stripped has an increased concentration cyclohexanone and cyclohexanone oxime, with no or only limited increase of the concentration cyclohexanone and cyclohexanone oxime in the aqueous medium obtained after stripping. This is advantageous since separation steps prior to stripping may be omitted or carried out to a lesser extent. Moreover, higher amounts of hydroxylammonium may be converted in the cyclohexanone oxime synthesis zone with no or only limited increase of concentration cyclohexanone and cyclohexanone oxime in the aqueous medium obtained after stripping, and entering the hydroxylammonium synthesis zone. A further advantage of the process according to the invention is that less steam may be used to obtain a desired decrease of the concentration cyclohexanone and cyclohexanone oxime. Another advantage is that increased amounts of cyclohexanone can be obtained in the vapor stream.

According to the invention the stripping is carried out at a pressure higher than 0.11 MPa. Preferably, the stripping is carried out at a pressure higher than 0.13 MPa, more preferably higher than 0.15 MPa, in particular higher than 0.20 MPa. By increasing the pressure, the efficiency of the reduction of the cyclohexanone and cyclohexanone oxime concentration in the aqueous medium is further increased. There is no specific upper limit for the pressure. The stripping may be carried out at a pressure lower than 1 MPa, usually lower than 0.6 MPa. The pressure may be adjusted by any suitable method, for example by using a pressure valve.

Preferably, the stripping is carried out at a temperature higher than 106° C., more preferably higher than 110° C., in particular higher than 115° C., in particular higher than 125° C. There is no specific upper limit for the temperature. The stripping may be carried out at a temperature lower than 185° C., usually lower than 160° C.

The stripping may be carried out in any suitable stripping zone wherein steam is passed through the aqueous medium. The aqueous medium and the steam may be contacted by any suitable method, preferably by contacting the aqueous medium and the steam in countercurrent flow. A vapor stream comprising steam and organic compounds discharges from the stripping zone.

The vapor stream may include organic compounds which were originally present in the aqueous medium prior to entering the stripping zone, e.g. cyclohexanone, and/or organic compounds which are formed in the stripping zone by conversion of cyclohexanone oxime into other products, in particular into cyclohexanone. Typically, the organic compounds in the vapor stream include cyclohexanone.

Preferably, the vapor stream discharging from the stripping zone has a pressure higher than 0.11 MPa, more preferably higher than 0.13 MPa, more preferably higher than 0.15 MPa, in particular higher than 0.20 MPa. There is no specific upper limit for the pressure of the vapor stream discharging from the stripping zone. The vapor stream discharging from the stripping zone may have a pressure lower than 1 MPa, usually lower than 0.6 MPa. Said pressures refer to the pressure of the vapor stream at the point where it discharges from the stripping zone.

Preferably, the vapor stream discharging from the stripping zone has a temperature higher than 106° C., more preferably higher than 110° C., in particular higher than 115° C., in particular higher than 125° C. There is no specific upper limit for the temperature of the vapor stream discharging from the stripping zone. The vapor stream discharging from the stripping zone may have a temperature below 185° C., usually below 160° C. Said temperatures refer to the temperature of the vapor stream at the point where it discharges from the stripping zone.

Preferably, the superficial gas velocity of said steam passing through the stripping zone is between 0.2 and 3 m/s, more preferably between 0.4 and 1.5 m/s. As used herein the superficial gas velocity refers to the volumetric steam flow (in m$^3$/s) divided by the free cross sectional area of the stripping zone (in m$^2$). The residence time of the aqueous medium in the stripping zone is preferably between 0.5 and 60 minutes.

The steam may be obtained from any source, for instance by evaporating water from the aqueous medium. Evaporating part of the water of the aqueous medium may be performed in the stripping zone. It is also possible to evaporate part of the water from the aqueous medium before the aqueous medium enters the stripping zone or after the aqueous medium has been discharged from the stripping zone. In a preferred embodiment, the process comprises obtaining said steam by evaporation of the water from the aqueous medium in an amount of 20-400 kg water per m$^3$ of aqueous medium, more preferably in an amount of 50-200 kg water per m$^3$ of the aqueous medium.

Any suitable vessel may be used as a stripping zone. Preferably, the stripping zone is a column. Preferably, such column is a plate column or a packed column. The plate column may be any suitable column fitted with plates, for instance sieve trays, bubble caps or valve trays.

In a preferred embodiment the aqueous medium contains phosphate, preferably between 2.0-8.0 mol phosphate per liter of aqueous medium. The phosphate may be present as $H_3PO_4$, $H_2PO_4^-$, $HPO_4^{2-}$ and/or $PO_4^{3-}$. Preferably, the aqueous medium is buffered. Preferably, the aqueous medium is an acidic aqueous medium. Preferably, the aqueous medium to be stripped has a pH of between 0 and 4, more preferably between 0.5 and 4. In a preferred embodiment, the aqueous medium to be stripped contains 2.0-8.0 mol phosphate, 0.5-8.0 mol ammonium ($NH_{4+}$) and 0.1-5.0 mol nitrate ($NO_3^-$) per liter of aqueous medium. As used herein the phosphate content refers to the joint content of $H_3PO_4$, $H_2PO_4^-$, $HPO_4^{2-}$ and $PO_4^{3-}$ per liter of medium. As used herein the aqueous medium to be stripped refers to the aqueous medium entering the stripping zone.

Preferably, the joint content of cyclohexanone oxime and cyclohexanone in the aqueous medium to be stripped is less than 0.5 wt. %, more preferably, less than 0.2 wt. %, in particular less than 0.1 wt. %, more in particular less than 0.05 wt. %, in particular less than 0.02 wt. %. Said weight percentages are given with respect to the weight of the aqueous medium. A lower joint content of cyclohexanone oxime and cyclohexanone has the advantage that the tendency for salt loss via the vapor stream is decreased.

The joint content of cyclohexanone and cyclohexanone oxime in the aqueous medium exiting the stripping zone may be less than 0.02 wt. %. Preferably, the joint content of cyclohexanone oxime and cyclohexanone in the aqueous medium exiting the stripping zone is less than 0.01 wt. %, more preferably less than 0.002 wt. %, in particular less than 0.0005 wt. %, more in particular less than 0.0002 wt. %, most preferably less than 0.0001 wt. %. Said weight percentages are given with respect to the weight of the aqueous medium exiting the stripping zone.

Advantageously, the process comprises causing heat exchange between the vapor discharge stream and a process liquid. This is an effective way for using heat of the vapor stream. Preferably, said process liquid is a process liquid in a production process for caprolactam. Examples of suitable process liquids include organic product comprising cyclohexanone oxime in an organic solvent, e.g. toluene, or an ammonium sulphate solution. Preferably, the process comprises withdrawing said organic product from the cyclohexanone oxime synthesis zone. Preferably, said heat exchange comprises feeding said vapor stream to a heat exchanger. In a preferred embodiment said heat exchanger is a reboiler of a distillation column, for instance a distillation column wherein cyclohexanone oxime is separated from an organic product comprising cyclohexanone and organic solvent, or a heat exchanger of a crystallizer, for instance a crystallizer wherein water is evaporated from an ammonium sulphate solution to effect crystallization of ammonium sulphate crystals.

Cyclohexanone may be separated from the vapor stream, for example by phase separation. Separated cyclohexanone may be recycled to the cyclohexanone oxime synthesis zone.

Generally, the concentration of hydroxylammonium in the aqueous medium entering the cyclohexanone oxime synthesis zone is higher than 0.8 mol/l. Preferably, the concentration hydroxylammonium in the aqueous medium entering the cyclohexanone oxime synthesis zone is higher than 1.0 mol/l, more preferably higher than 1.2 mol/l, more preferably higher than 1.4 mol/l, in particular higher than 1.6 mol/l. Increasing the concentration hydroxylammonium in the aqueous medium entering the cyclohexanone oxime synthesis zone is advantageous, since it may for instance result in an increased conversion of hydroxylammonium and/or smaller losses of hydroxylammonium by decomposition. An increased concentration hydroxylammonium in the aqueous medium entering the cyclohexanone oxime synthesis zone may for instance be achieved by increasing the residence time in the hydroxylammonium synthesis zone and/or by increasing the nitrate concentration in the aqueous medium entering the hydroxylammonium synthesis zone. There is no specific upper limit for the concentration hydroxylammonium in the aqueous medium entering the cyclohexanone oxime synthesis zone. Generally, the concentration hydroxylammonium in the aqueous medium entering the cyclohexanone oxime synthesis zone is below 2.5 mol/l.

We found that an increase of the concentration hydroxylammonium in the aqueous medium entering the cyclohexanone oxime synthesis zone may result in an increase of the concentration of organic contaminants, in particular cyclohexanone and cyclohexanone oxime, in the aqueous medium exiting the cyclohexanone oxime synthesis zone. The increased amounts of organic compounds can advantageously be reduced by the process according to the invention.

In the cyclohexanone oxime synthesis zone, hydroxylammonium is reacted with cyclohexanone to form cyclohexanone oxime, preferably in the presence of an organic solvent. Any suitable organic solvent may be used in which cyclohexanone and cyclohexanone oxime may be dissolved. Preferably, the organic solvent is selected from the group consisting of benzene, toluene, xylene, methylcyclopentane, cyclohexane and mixtures thereof. Most preferably, the organic solvent is toluene. A suitable process is for instance described in GB-A-1,138,750. In a preferred embodiment, the reaction of hydroxylammonium with cyclohexanone is effected by contacting the aqueous medium and an organic stream comprising cyclohexanone and the organic solvent in countercurrent flow. The cyclohexanone oxime produced may be discharged from the cyclohexanone oxime synthesis zone by any suitable method, preferably by withdrawing an organic product from the cyclohexanone oxime synthesis zone, said organic product comprising the cyclohexanone oxime and the organic solvent. The organic solvent and the cyclohexanone may be introduced into the cyclohexanone oxime synthesis zone at any suitable point, preferably downstream of the point where the organic product is withdrawn from the cyclohexanone oxime synthesis zone (seen in the direction of flow of the aqueous medium). Most preferably, the organic solvent and the cyclohexanone are introduced into the cyclohexanone oxime synthesis zone downstream of the point where the organic product is discharged from the cyclohexanone oxime synthesis zone, and the organic solvent is introduced downstream of the point where the cyclohexanone is introduced into the cyclohexanone oxime synthesis zone (seen in the direction of flow of the aqueous medium). This embodiment has the advantage that extraction of residual amounts of cyclohexanone and cyclohexanone oxime from the aqueous medium is improved. As used herein, the zone between the point where the organic product leaves the cyclohexanone oxime synthesis zone and the point where the cyclohexanone is introduced into the cyclohexanone oxime synthesis zone is also referred to as reaction zone. As used herein the zone between the point where the cyclohexanone is introduced into the cyclohexanone oxime synthesis zone and the point where the organic solvent is introduced into the cyclohexanone oxime synthesis zone is also referred to as extraction zone. For the reaction zone and extraction zone, use may be made of known types of counterflow reactors, such as for instance pulsed columns filled with packing bodies or rotating disc reactors. It is also possible to use a system comprising a number, e.g. 3 to 6, of series-connected reactors equipped with stirrers, each of these reactors also being provided with a liquid-liquid separator. The cyclohexanone oxime synthesis zone is preferably operated at a temperature between 40 to 150° C. Preferably, the reaction medium entering the cyclohexanone oxime synthesis zone has a pH of between 1 and 6, more preferably between 1.5 and 4.

In the hydroxylammonium synthesis zone hydroxylammonium is formed by catalytic reduction of nitrate or nitrogen oxide with hydrogen. The hydroxylammonium synthesis zone may be operated at a temperature ranging from 20 to 100° C., preferably 30-90° C., more preferably 40-65° C., and at atmospheric, sub-atmospheric or elevated pressures, preferably between 0.1 and 5 MPa, more preferably between 0.3 and 3 MPa, and in particular between 0.5 and 2 MPa (hydrogen partial pressure). Preferably, the pH in the hydroxylammonium synthesis zone is between 0.5 and 6, more preferably between 1 and 4. The catalyst employed in this zone is generally present in a range of between 1 to 25 wt. %, preferably between 5 to 15 wt. % of a precious metal, relative to total weight of support plus catalyst. Preferably, the catalyst is a palladium containing catalyst, for instance a palladium or a palladium-platinum catalyst, present on a support, such as for instance carbon or alumina support. Generally, the catalyst is present in the hydroxylammonium synthesis zone in an amount of 0.2-5 wt. % relative to the total liquid weight in the hydroxylammonium reactor vessel(s). The hydroxylammonium synthesis zone is not limited to a specific reactor. A reactor with a mechanical stirrer may be used. Preferably, the reactor is column, preferably a bubble column. An example of a suitable bubble column is described in NL-A-6908934.

DESCRIPTION OF AN EMBODIMENT

Figure 1:
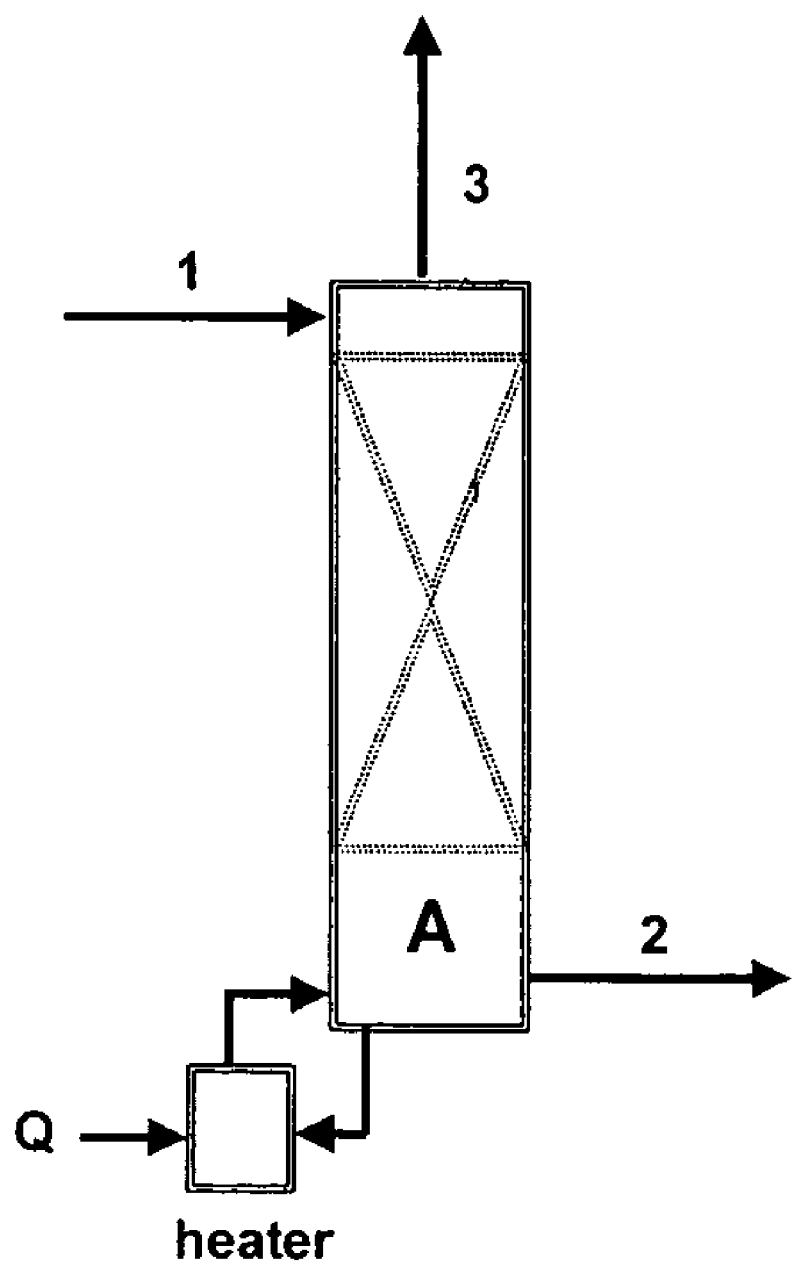
FIG. 1 is a schematic diagram of an embodiment of a stripping column.

Referring to FIG. 1, A represents a stripping column. To zone A the aqueous medium containing cyclohexanone and cyclohexanone oxime is fed via line 1. The stripped aqueous medium containing a reduced amount of cyclohexanone and cyclohexanone oxime leaves the stripping zone A via line 2. Steam is generated at the bottom of the stripping column by heat supply (Q) via a heater. Steam contacts the aqueous medium in counter current flow and at the top of the column a vapor stream comprising steam and cyclohexanone is discharged from the stripping column through line 3.

Figure 2:
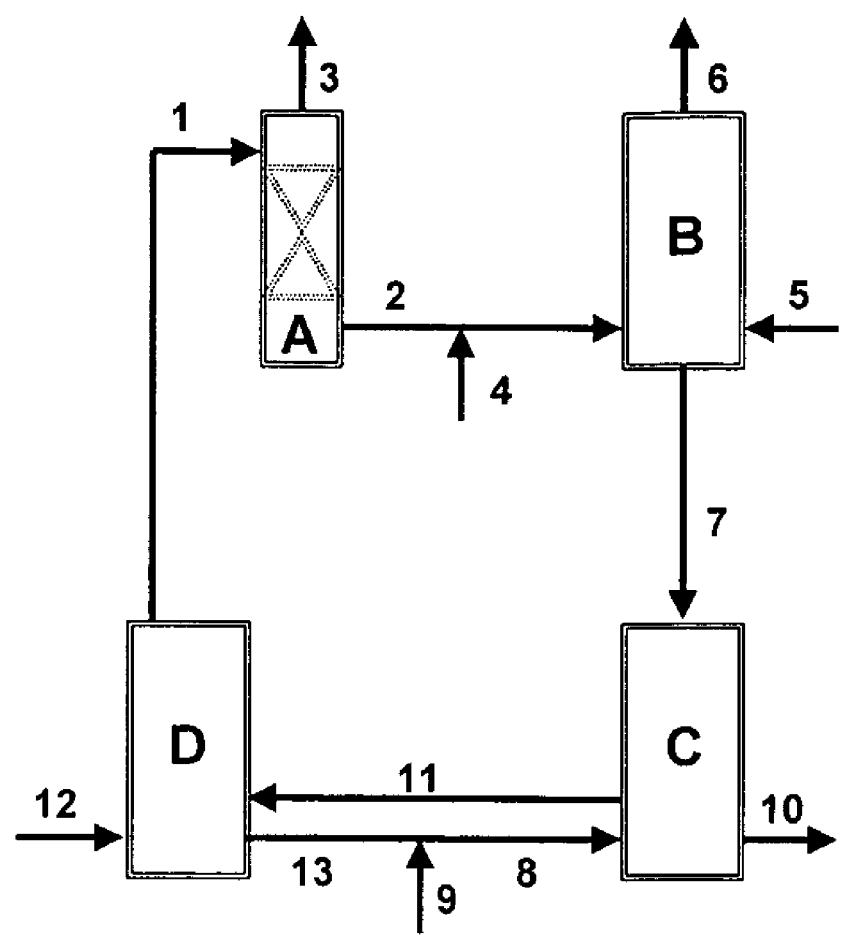
FIG. 2 is a schematic diagram of an embodiment of a process according to the present invention.

Referring to FIG. 2, A represents the stripping zone as described under FIG. 1. The aqueous medium, discharged from the stripping zone A, is recycled to a hydroxylammonium synthesis zone B via line 2. The aqueous medium may be enriched with nitrate ions by addition of nitric acid and/or absorption of nitrous gases through line 4. In zone B hydroxylammonium is formed by catalytic reduction of nitrate with hydrogen. Hydrogen is fed via line 5 to zone B, containing catalyst and nitrate ions; unreacted hydrogen is discharged, with any other gases, via line 6. After being enriched in hydroxylammonium, in zone B, the aqueous medium is passed to the cyclohexanone oxime synthesis zone via line 7. The cyclohexanone oxime synthesis zone comprises reaction zone C and extraction zone D. The cyclohexanone to be converted into cyclohexanone oxime in zone C is fed to zone C in an organic solvent through line 8. The cyclohexanone is introduced into the organic solvent via line 9. The largest part of cyclohexanone oxime produced and dissolved in the organic solvent is removed from the system via line 10. The aqueous medium is passed from reaction zone C to extraction zone D through line 11. Upon passing reaction zone C, the hydroxylammonium content of the aqueous medium has been reduced by reaction and contains small amounts of cyclohexanone and cyclohexanone oxime. The organic solvent enters extraction zone D through line 12. Within extraction zone D, residual cyclohexanone oxime dissolved in an organic solvent is removed from the aqueous medium through line 13. Through line 1, the aqueous medium leaves the extraction zone D to be fed to the stripping zone A, completing the cycle. The process is carried out continuously.

The invention will be elucidated by the following examples without being limited thereto.

EXAMPLES AND COMPARATIVE EXPERIMENTS

Comparative Experiment A

An aqueous medium is fed to the upper part of a stripping column, a column equipped with 21 sieve trays, a feeding point at the top of the column and a reboiler at the bottom. The dimensions of the stripping column are as follows: a height of 0.8 m and a diameter of 0.025 m. The aqueous medium entering the stripping column (10 liter/hour) comprises:

16% by weight of $H_3PO_4$
17% by weight of $NH_4NO_3$
7% by weight of $NH_4H_2PO_4$
0.8% by weight of hydroxylammonium phosphate
0.1% by weight of cyclohexanone oxime and cyclohexanone.

The stripping column is operated under atmospheric pressure, i.e. the vapor stream leaving the column had a pressure of 0.1 MPa and a temperature of 106° C. Steam is generated in the lower part of the column by evaporation part of the acidic aqueous medium (1 kg per hour). Steam comprising water and cyclohexanone leaves the stripping column in an amount of (1 kg per hour). The residence time of the acidic aqueous medium in the column is 5 minutes. The joint content of cyclohexanone oxime and cyclohexanone in the aqueous medium leaving the column is 0.012 wt. %. The amount of cyclohexanone leaving the column with the steam is 0.9 wt. %. The results are given in Table I, Example A.

Examples I-IV

The same experiment as described in experiment A is performed except that the stripping column is operated under pressures of 0.12, 0.15, 0.5 and 1.0 MPa and temperatures of 110, 116, 157 and 185° C., respectively. The joint content of cyclohexanone oxime and cyclohexanone in the aqueous medium leaving the column is 0.006, 0.002, 0.0004 and <0.0001 wt. %, respectively. The amount of cyclohexanone leaving the column with the steam is 0.9, 1.0, 1.0 and 1.0 wt. %, respectively. The results (given in Table I) show that increasing the pressure results in a decreased joint content of cyclohexanone oxime and cyclohexanone in the aqueous medium leaving the column, and an increased amount of cyclohexanone in the steam.

Reference Experiment B

The same experiment as described in comparative experiment A is performed except that the joint content of cyclohexanone and cyclohexanone oxime in the aqueous medium entering the stripping column is 0.025% by weight. The joint content of cyclohexanone oxime and cyclohexanone in the aqueous medium leaving the column is 0.003 wt. %. The amount of cyclohexanone leaving the column with the steam is 0.2 wt. %. The results are given in Table II.

Examples V-X

The same experiment as described in experiment B is performed except that the stripping column is operated under pressures of 0.12, 0.16, 0.17, 0.21, 0.27 and 0.5 MPa and temperatures of 110, 118, 121, 127, 135 and 157° C., respectively. The joint content of cyclohexanone oxime and cyclohexanone in the aqueous medium leaving the column is 0.001, 0.0005, 0.0003, 0.0002, <0.0001 and <0.0001 wt. %, respectively. The results (given in Table II) show that further increased pressures result in a further decreased joint content of cyclohexanone oxime and cyclohexanone in the aqueous medium leaving the column.

Experiments 1-3

In these experiments the embodiment as illustrated in FIG. 2 was used to show the effect of an increasing concentration hydroxylammonium in the aqueous medium entering the cyclohexanone oxime synthesis zone.

Experiment 1

In hydroxylammonium synthesis zone B (containing a catalyst (8 wt. % Pd and 2 wt. % Pt supported on carbon), operated at a temperature of 55° C. at a pressure of 1 MPa (hydrogen partial pressure)) an aqueous medium having the following composition:

1.30 mol $NH_3OH.H_2PO_4$
1.38 mol $NH_4H_2PO_4$
0.665 mol $H_3PO_4$
1.73 mol $NH_4NO_3$
39.9 mol $H_2$ (corresponding to a concentration hydroxylammonium in the aqueous medium of 1.3 mol/l, and a phosphate concentration of 3.34 mol/l) was produced per unit of time, and continuously fed to reaction zone C (a pulsed packed column, operated at 55° C.), together with cyclohexanone and toluene. The molar ratio of hydroxylammonium fed to the cyclohexanone oxime synthesis zone per unit of time to cyclohexanone fed to the cyclohexanone oxime synthesis zone per unit of time, i.e. the ratio hydroxylammonium (in mol/s)/cyclohexanone (in mol/s) was 0.95. Substantially all hydroxyl ammonium was reacted to form cyclohexanone oxime. Cyclohexanone oxime dissolved in toluene was withdrawn from zone C, the cyclohexanone concentration being 38 wt. % (relative to the sum weight of toluene+cyclohexanone oxime). The aqueous medium exiting zone C was fed to extraction zone D (a pulsed packed column, operated at 70° C.), together with toluene.

The joint content of cyclohexanone and cyclohexanone oxime in the aqueous medium exiting extraction zone D was 0.0043 wt. % (43 ppm).

Experiment 2

In this example all conditions were the same as in the previous examples, except that the aqueous medium exiting hydroxylammonium synthesis zone B and entering reaction zone C had the following composition 1.50 mol $NH_3OH.H_2PO_4$
1.45 mol $NH_4H_2PO_4$
0.39 mol $H_3PO_4$
1.65 mol $NH_4NO_3$
39.8 mol $H_2O$ (corresponding to a concentration hydroxylammonium in the aqueous medium of 1.5 mol/l, and a phosphate concentration of 3.34 mol/l). The joint content of cyclohexanone and cyclohexanone oxime in the aqueous medium exiting extraction zone D was 0.0218 wt. % (218 ppm).

Experiment 3

In this example all conditions were the same as in the previous examples, except that the aqueous medium exiting hydroxylammonium synthesis zone B and entering reaction zone C had the following composition 1.60 mol $NH_3OH.H_2PO_4$
1.45 mol $NH_4H_2PO_4$
0.30 mol $H_3PO_4$
1.65 mol $NH_4NO_3$
39.6 mol $H_2O$ (corresponding to a concentration hydroxylammonium in the aqueous medium of 1.6 mol/l, and a phosphate concentration of 3.34 mol/l). The joint content of cyclohexanone and cyclohexanone oxime in the aqueous medium exiting extraction zone D was 0.0277 wt. % (277 ppm).

Table III gives an overview of experiments 1 to 3. These experiments show that an increase of the concentration hydroxylammonium in the aqueous medium entering the cyclohexanone oxime synthesis zone results in an increase of the concentration cyclohexanone and cyclohexanone oxime in the aqueous medium exiting the cyclohexanone oxime synthesis zone. The increased concentration of cyclohexanone and cyclohexanone oxime can advantageously be separated from the aqueous medium by the improved stripping process according to the invention.

TABLE I

Result of stripping of an aqueous medium comprising 1000 ppm of cyclohexanone oxime and cyclohexanone

| Example | pressure of vapor stream (Mpa) | temperature in ° C. | Joint content of cyclohexanone oxime and cyclohexanone in the aqueous medium after stripping (in wt. %) | concentration cyclohexanone in the steam after stripping in wt. % |
|---|---|---|---|---|
| A | 0.10 | 106 | 0.012 | 0.9 |
| I | 0.12 | 110 | 0.006 | 0.9 |
| II | 0.15 | 116 | 0.002 | 1.0 |
| III | 0.5 | 157 | 0.0004 | 1.0 |
| IV | 1.0 | 185 | <0.0001 | 1.0 |

TABLE II

Result of stripping of an aqueous medium comprising 250 ppm of cyclohexanone oxime and cyclohexanone

| Example | pressure of vapor stream (Mpa) | temperature in ° C. | Joint content of cyclohexanone oxime and cyclohexanone in the aqueous medium after stripping (in wt. %) | concentration cyclohexanone in the steam after stripping in wt. % |
|---|---|---|---|---|
| B | 0.10 | 106 | 0.003 | 0.2 |
| V | 0.12 | 110 | 0.001 | 0.25 |
| VI | 0.16 | 118 | 0.0005 | 0.25 |
| VII | 0.17 | 121 | 0.0003 | 0.25 |
| VIII | 0.21 | 127 | 0.0002 | 0.25 |
| IX | 0.27 | 135 | <0.0001 | 0.25 |
| X | 0.5 | 157 | <0.0001 | 0.25 |

TABLE III overview of results of experiments 1 to 3

| Exp. | Concentration hydroxylammonium in aqueous medium entering cyclohexanone oxime synthesis zone (mol/l) | Joint content cyclohexanone and cyclohexanone oxime in aqueous medium exiting cyclohexanone oxime synthesis zone (ppm) |
|---|---|---|
| 1 | 1.3 | 43 |
| 2 | 1.5 | 218 |
| 3 | 1.6 | 277 |

The invention claimed is:

1. A process for preparing cyclohexanone oxime comprising:
    passing an aqueous medium containing phosphate from a hydroxylammonium synthesis zone to a cyclohexanone oxime synthesis zone, from the cyclohexanone oxime synthesis zone to a stripping zone and from the stripping zone back to the hydroxylammonium synthesis zone,
    in said hydroxylammonium synthesis zone, preparing hydroxylammonium by catalytically reducing nitrate or nitrogen oxide with hydrogen;
    in said cyclohexanone oxime synthesis zone, preparing cyclohexanone oxime by reacting hydroxylammonium with cyclohexanone;
    in said stripping zone, stripping the aqueous medium with steam; wherein said stripping is carried out at a pressure higher than 0.11 MPa.

2. The process according to claim 1, wherein the concentration of hydroxylammonium in the aqueous medium entering the cyclohexanone oxime synthesis zone is higher than 1.0 mol/l.

3. The process according to claim 2, wherein the concentration of hydroxylammonium in the aqueous medium entering the cyclohexanone oxime synthesis zone is higher than 1.4 mol/l.

4. The process according to claim 1, wherein the stripping is carried out at a pressure higher than 0.15 MPa.

5. The process according to claim 1, wherein the superficial gas velocity of said steam is between 0.2 and 3 m/s.

6. The process according to claim 1, wherein the process comprises obtaining said steam by evaporating water from the aqueous medium.

7. The process according to claim 1, wherein said stripping is carried out in a column.

8. The process according to claim 1, wherein said column is a plate column or a packed column.

9. The process according to claim 1, wherein the aqueous medium is an acidic aqueous medium.

10. The process according to claim 1, wherein the aqueous medium to be stripped has a pH of between 0 and 4.

11. The process according to claim 1, wherein the aqueous medium to be stripped contains 2.0-8.0 mol/l of phosphate, 0.5-8.0 mol/l of ammonium and 0.1-5.0 mol/l of nitrate.

12. The process according to claim 1, wherein the joint content of cyclohexanone oxime and cyclohexanone in the aqueous medium to be stripped is less than 0.5 wt. %.

13. The process according to claim 1, wherein said stripping is carried out in a stripping zone, and wherein the process comprises discharging a vapor stream from said stripping zone, said vapor stream having a pressure higher than 0.11 MPa.

14. The process according to claim 13, wherein said vapor stream comprises steam and cyclohexanone.

15. The process according to claim 13, wherein the process comprises exchanging heat of the vapor stream to a process liquid.

16. The process according to claim 15, wherein said process liquid is a process liquid in a production process for caprolactam.

17. The process according to claim 16, wherein said process liquid is mixture comprising toluene and cyclohexanone oxime.

* * * * *